US012640244B2

(12) United States Patent
Margarito et al.

(10) Patent No.: US 12,640,244 B2
(45) Date of Patent: May 26, 2026

(54) SYSTEM AND METHOD TO PREDICT PERSONALITY TYPE TO DELIVER CPAP THERAPY SUPPORT

(71) Applicant: KONINKLIJKE PHILIPS N.V., Eindhoven (NL)

(72) Inventors: Jenny Margarito, Eindhoven (NL); Boris Emmanuel Rachmund De Ruyter, Peer (BE); Jan Martijn Krans, Den Bosch (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 104 days.

(21) Appl. No.: 18/233,992

(22) Filed: Aug. 15, 2023

(65) Prior Publication Data

US 2024/0071587 A1      Feb. 29, 2024

(30) Foreign Application Priority Data

Aug. 26, 2022     (EP) ..................................... 22192452

(51) Int. Cl.
G16H 20/00          (2018.01)
G16H 50/20          (2018.01)

(52) U.S. Cl.
CPC .............. G16H 20/00 (2018.01); G16H 50/20 (2018.01)

(58) Field of Classification Search
None
See application file for complete search history.

(56) References Cited

U.S. PATENT DOCUMENTS

| | | | |
|---|---|---|---|
| 9,449,287 B2 | 9/2016 | Gunjan | |
| 11,262,984 B2 | 3/2022 | Svyatkovskiy et al. | |
| 11,363,984 B2 * | 6/2022 | Stern .................... | A61B 5/4818 |
| 11,769,576 B2 * | 9/2023 | Moturu .................. | G16H 50/30 |
| | | | 705/2 |
| 2012/0284080 A1 | 11/2012 | De Oliveira et al. | |
| 2014/0335490 A1 * | 11/2014 | Baarman ............... | A61B 5/1118 |
| | | | 434/236 |
| 2015/0278590 A1 | 10/2015 | Gunjan | |

(Continued)

OTHER PUBLICATIONS

Grande et al., "The type-D scale (DS14)—Norms and prevalence of type-D personality in a population-based representative sample in Germany", Personality and Individual Differences 48 (2010), pp. 935-939.

(Continued)

*Primary Examiner* — Robert A Sorey
(74) *Attorney, Agent, or Firm* — Brynne J. Corcoran

(57) ABSTRACT

Systems, apparatuses, and methods include technology to provide guidance to a patient receiving obstructive sleep apnea treatment. For example, such technology is configured to extract one or more features describing mobile apps usage based on one or more mobile apps logs from a mobile device. A personality type of the patient is determined based on processing the one or more features describing mobile apps usage. A treatment guidance for the patient is determined based on the personality type, where the treatment guidance comprises a first set of messages for the patient in response to a first personality type and a different second set of messages for the patient in response to a different second personality type. The treatment guidance for the patient is communicated to the mobile device associated with the patient receiving obstructive sleep apnea treatment.

14 Claims, 6 Drawing Sheets

(56) References Cited

U.S. PATENT DOCUMENTS

| | | |
|---|---|---|
| 2017/0004260 A1 | 1/2017 | Moturu et al. |
| 2018/0075483 A1 | 3/2018 | Boyarshinov |
| 2021/0391083 A1 | 12/2021 | Moturu et al. |
| 2022/0215959 A1* | 7/2022 | Kaigler ................. A61M 21/02 |
| 2022/0238228 A1 | 7/2022 | Batista |
| 2022/0246293 A1 | 8/2022 | Peake |
| 2023/0245780 A1 | 8/2023 | Molony et al. |
| 2024/0050032 A1* | 2/2024 | Sundaram ............ A61B 5/7275 |
| 2024/0296958 A1* | 9/2024 | Chanan ................. G16H 10/60 |

OTHER PUBLICATIONS

Punjabi, "The Epidemiology of Adult Obstructive Sleep Apnea," in Proceedings of the American Thoracic Society, vol. 5. (2008), pp. 136-143.

Beierle et al., "What data are smartphone users willing to share with researchers?", Journal of Ambient Intelligence and Humanized Computing (2020) 11, pp. 2277-2289.

Stachl et al., "Predicting personality from patterns of behavior collected with smartphones," in Proceedings of the National Academy of Sciences , vol. 117, No. 30, Jul. 28, 2020, pp. 17680-17677.

Cayanan et al., "A review of psychosocial factors and personality in the treatment of obstructive sleep apnoea", No. 4 in the Series "Sleep Disordered Breathing", Eur Respir Rev 2019; 28: 190005 pp. 1-12, (2019).

Kambham, "Predicting personality traits using smartphone sensor data and app usage data," in 2018 IEEE 9th Annual Information Technology, Electronics and Mobile Communication Conference (IEMCON). , 2018.

Maragakis, "Eysenck Personality questionnaire-revised.," The Wiley Encyclopedia of Personality and Individual Differences: Measurement and Assessment, vol. II, First Edition, 2020, pp. 283-286.

Gao et al., "PersonalitySensing: A Multi-View Multi-Task Learning Approach for Personality Detection based on Smartphone Usage", Poster Session D2: Emerging Multimedia Applications & Emotional and Social Signals in. Multimedia, MM '20, Oct. 12-16, 2020, Seattle, WA, USA, pp. 2862-2870.

* cited by examiner

400

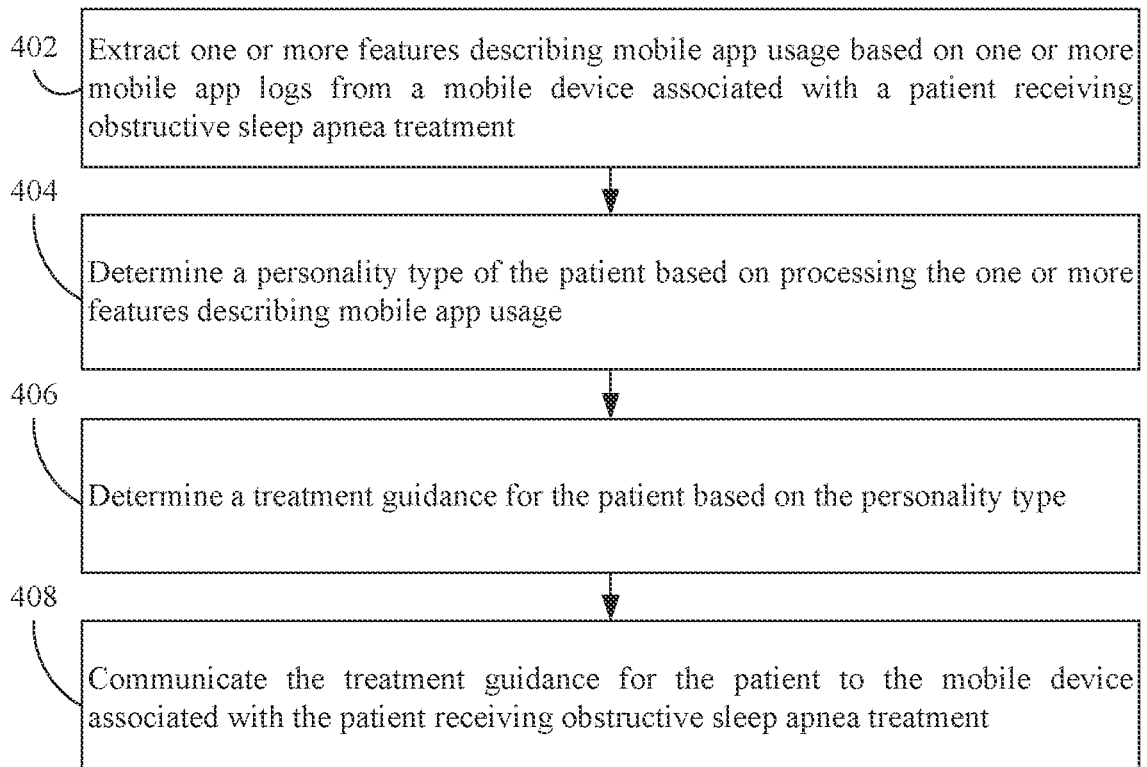

402  Extract one or more features describing mobile app usage based on one or more mobile app logs from a mobile device associated with a patient receiving obstructive sleep apnea treatment 404  Determine a personality type of the patient based on processing the one or more features describing mobile app usage 406  Determine a treatment guidance for the patient based on the personality type 408  Communicate the treatment guidance for the patient to the mobile device associated with the patient receiving obstructive sleep apnea treatment

FIG. 4

Computer Program Product 600

Machine-readable Storage 602

Logic 604

CPAP Therapy Management System 100

Memory 704

Logic 706

Processor 702

800

Logic

804

Substrate(s)

802

SYSTEM AND METHOD TO PREDICT PERSONALITY TYPE TO DELIVER CPAP THERAPY SUPPORT

CROSS-REFERENCE TO PRIOR APPLICATION

This application claims the benefit of European Patent Application No. 22192452.5, filed on Aug. 26, 2022. This application is hereby incorporated by reference herein.

FIELD

The following relates generally to medical therapy. More particularly, embodiments herein relate to delivering continuous positive airway pressure (CPAP) therapy support based on a prediction of a patient's personality type.

BACKGROUND

Obstructive sleep apnea (OSA) is a chronic condition characterized by frequent episodes of upper airway collapse during sleep. The health consequences of obstructive sleep apnea are numerous. If left untreated, it often leads to excessive daytime sleepiness, cognitive dysfunction, impaired work performance, and decrements in health-related quality of life. OSA is being increasingly recognized as an important cause of medical morbidity and mortality.

Effective treatment of OSA is primarily determined by adherence to one of three selected interventions of continuous positive airway pressure (CPAP), a mandibular advancement device (MAD) and/or weight loss therapy. Continuous positive airway pressure (CPAP) therapy is the most common treatment but adherence is poor (e.g., with ~50% of patients being unable to use CPAP).

In several studies it has been shown that personality plays a role in CPAP adherence. In a recent comprehensive review, the impact of type-D personality on CPAP adherence was associated with poorer adherence and treatment outcomes due to negative affectivity, social inhibition, unhealthy lifestyle, and a reluctance to consult and/or follow medical advice. Patients more likely to adhere to CPAP therapy demonstrated a high internal locus of control, high self-efficacy, were self-referred for treatment and had active coping skills. A conservative approach suggests that personality and depression should still be considered as potential predictors of CPAP compliance that require attention when measured as being compromised to ensure the appropriate interventions are applied. Therefore, if a patient is identified with unfavourable personality traits (e.g., personality type-D or low readiness or self-efficacy) this may to be addressed prior to initiating therapy. This early identification of potential difficulties may be used to enhance treatment adherence while the maintenance of CPAP therapy will potentially enhance positive psychosocial wellbeing. Clinicians may execute manual personality tests before initiating the therapy to be able to determine if patient will be compliant and based on that to define which kind of support the patient needs in order to become compliant and stay compliant. Yet, such questionnaires are often lengthy and therefore are not often utilized by clinicians. Some examples of tests which are used for identifying personality are: Eysenck Personality Questionnaire (EPQ) and the Revised NEO Personality Inventory (NEO PI-R).

Some techniques may be used to assess personality by analysing information collected from different sources. Such sources may include social media, call detail record, email etc. using DISC (dominance, inducement, submission, and compliance) profiling and Big Five personality techniques (openness, conscientiousness, extraversion, agreeableness, and neuroticism).

One method provides OSA patients with personalized reports about their therapy. The content of the report is personalized based on the expressed preference of the patient. For example, such a preference is expressed by the patient selecting one of four descriptions of how they would prefer to receive care. Each selection corresponds to one of for personality types (e.g., A fighter, B analyst, C optimist and D sensitive). Such a personalized report has been shown to improve the adherence of the patients to the OSA therapy, thus proving the benefit of personalizing interaction for improving adherence to therapy. Yet, the personalization is only based on answer to a single question after therapy already started.

Additionally, several studies have discussed using smartphone data including apps usage, location, and motion information to identify general personality traits.

SUMMARY

As discussed above, it is currently challenging to use execute personality tests before initiating CPAP therapy. Adherence to CPAP therapy is dependent on the personality type of the patient. Assessment of personality type is essential to be performed prior to the therapy in order to provide adequate support to the patient initiating the therapy. Typically, personality type assessment requires filling of questionnaires, which is a very time consuming task for both patient and clinician, because such questionnaires are often very lengthy. Therefore, the personality assessment is most times not performed at all.

Therefore, it would be desirable to be able to identify the personality traits of an OSA patient prior to therapy in an automatic manner and to use such information for providing guidance and support for get acquainted with the therapy.

The following discloses certain improvements to overcome these problems and others.

In the present disclosure, procedures are described that detect personality type from a mobile device (e.g., information related to the usage of mobile apps, such as app logs, browsing information, type of content visualized in the app as well as frequency, duration and time of the usage, the like, and/or combinations thereof). Such procedures would minimize the effort required from assessing the user/patient personality, would provide profiling information useful to personalize the support to the patient based on his characteristics, and provide a non-obtrusive and low cost solution for helping to increase the adherence to the therapy. For example, procedures are described that utilize smartphone data related to a patient's habits and their response to OSA diagnosis as well as initial support provided via messaging for assessing the patient's personality traits in an automatic manner, and use an automatically determined personality type information for customizing content of automatic messages sent to the patient aiming at increasing CPAP adherence.

Systems, apparatuses, and methods described herein include technology to provide guidance to a patient receiving obstructive sleep apnea treatment. For example, such technology is configured to extract one or more features describing mobile apps usage based on one or more mobile apps logs from a mobile device. A personality type of the patient is determined based on processing the one or more features describing mobile apps usage. A treatment guidance for the patient is determined based on the personality type, where the treatment guidance comprises a first set of messages for the patient in response to a first personality type and a different second set of messages for the patient in response to a different second personality type. The treatment guidance for the patient is communicated to the mobile device associated with the patient receiving obstructive sleep apnea treatment.

In one aspect a therapy management system includes a processor and a memory communicatively coupled to the processor. The memory stores logic that includes instructions executable by the processor, which when executed by the processor, cause the processor to extract, via a personality type feature extractor, one or more features describing mobile apps usage based on one or more mobile apps logs from a mobile device associated with a patient receiving obstructive sleep apnea treatment. A personality type of the patient is determined, via a personality type detector, based on processing the one or more features describing mobile apps usage from the personality type feature extractor. A treatment guidance for the patient is determined, via an automatic messages generator, based on the personality type from the personality type detector, where the treatment guidance includes a first set of messages for the patient in response to a first personality type and a different second set of messages for the patient in response to a different second personality type. The treatment guidance for the patient is communicated, via the automatic messages generator, to the mobile device associated with the patient receiving obstructive sleep apnea treatment.

In another aspect, a computer readable medium includes a set of instructions, which when executed by a computing device, cause the computing device to extract, via a personality type feature extractor, one or more features describing mobile apps usage based on one or more mobile apps logs from a mobile device associated with a patient receiving obstructive sleep apnea treatment. A personality type of the patient is determined, via a personality type detector, based on processing the one or more features describing mobile apps usage from the personality type feature extractor. A treatment guidance for the patient is determined, via an automatic messages generator, based on the personality type from the personality type detector, where the treatment guidance includes a first set of messages for the patient in response to a first personality type and a different second set of messages for the patient in response to a different second personality type. The treatment guidance for the patient is communicated, via the automatic messages generator, to the mobile device associated with the patient receiving obstructive sleep apnea treatment.

In yet another aspect, a therapy management method (500), includes operations to extract, via a personality type feature extractor, one or more features describing mobile apps usage based on one or more mobile apps logs from a mobile device associated with a patient receiving obstructive sleep apnea treatment. A personality type of the patient is determined, via a personality type detector, based on processing the one or more features describing mobile apps usage from the personality type feature extractor. A treatment guidance for the patient is determined, via an automatic messages generator, based on the personality type from the personality type detector, where the treatment guidance includes a first set of messages for the patient in response to a first personality type and a different second set of messages for the patient in response to a different second personality type. The treatment guidance for the patient is communicated, via the automatic messages generator, to the mobile device associated with the patient receiving obstructive sleep apnea treatment.

It should be appreciated that all combinations of the foregoing concepts and additional concepts discussed in greater detail below (provided such concepts are not mutually inconsistent) are contemplated as being part of the subject matter disclosed herein. In particular, all combinations of claimed subject matter appearing at the end of this disclosure are contemplated as being part of the subject matter disclosed herein. It should also be appreciated that terminology explicitly employed herein that also may appear in any disclosure incorporated by reference should be accorded a meaning most consistent with the particular concepts disclosed herein.

These and other aspects of the various embodiments will be apparent from and elucidated with reference to the embodiment(s) described hereinafter.

BRIEF DESCRIPTION OF THE DRAWINGS

The various advantages of the embodiments will become apparent to one skilled in the art by reading the following specification and appended claims, and by referencing the following drawings, in which:

FIG. 4 is an illustration of a flowchart of a further method for monitoring and/or management of CPAP therapy according to an embodiment;

DETAILED DESCRIPTION

As will be described in greater detail below, in some implementations discussed herein, an automated tool may advantageously be used to address parts of the challenges in delivering CPAP therapy support based on a prediction of a patient's personality type.

Figure 1:
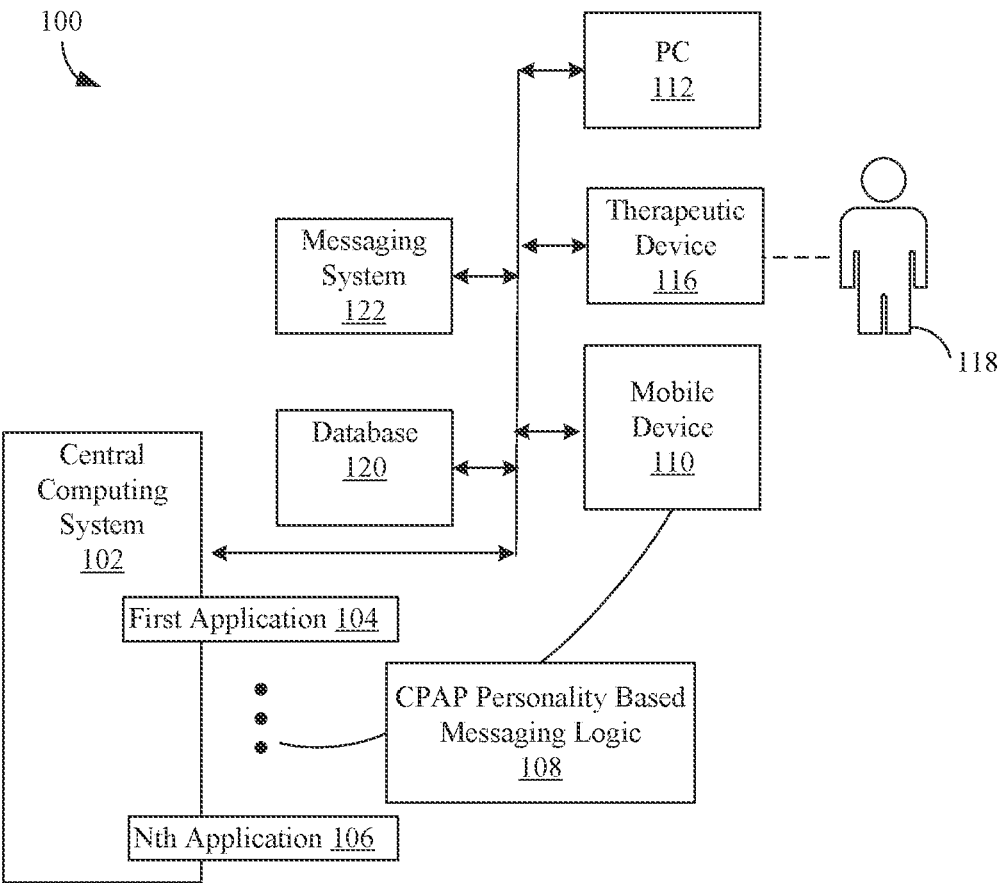
FIG. 1 is an illustration of a block diagram of an example CPAP therapy management system according to an embodiment.

FIG. 1 is an illustration of a block diagram of an example CPAP therapy management system 100 according to an embodiment. For example, the CPAP therapy management system 100 may be centralized or may be distributed and may include some or all elements and components of one or more computers or computer systems.

In the illustrated implementation, the CPAP therapy management system 100 includes a number of individual components, which together provide a sleep disordered breathing treatment and self-management mechanism. As described in greater detail herein, the CPAP therapy management system 100 provides a mechanism for a patient suffering from OSA to manage their treatment by providing education and feedback regarding their disease and their specific therapy that is automatically customized/personalized based on an automatically determined personality type. Advantageously, such operations to provide education and feedback that is automatically customized/personalized based on an automatically determined personality type typically will increasing therapy compliance.

For example, the CPAP therapy management system 100 may include a central computing system 102. In some implementations, the central computing system 102 may be embodied as a server computer or a plurality of server computers (e.g., interconnected to form a server cluster, cloud computing resource, the like, and/or combinations thereof).

In some implementations, a first application 104 though an Nth application 106, which may include a CPAP personality based messaging logic 108, may be associated with the central computing system 102. Additionally, or alternatively, all or portions of the CPAP personality based messaging logic 108 may be associated with another computing device (e.g., a mobile device 110). The operations of the CPAP personality based messaging logic 108 to trigger personality based therapy notifications and/or instructions to a patient will be described in greater detail below.

Additionally, or alternatively, the CPAP therapy management system 100 may include the mobile device 110, a personal computer 112, a therapeutic device 116, a database 120, a messaging system 122, the like, and/or combinations thereof. For example, the central computing system 102, the mobile device 110, the personal computer 112, the therapeutic device 116, the database 120, and/or the messaging system 122 may be in communication with one another via Internet based communication, cloud based communication, wired communication, wireless communication, the like, and/or combinations thereof.

In an example, the mobile device 110 may be utilized to enter patient data to the database 120. For example, the mobile device 110 may determine measured patient data (e.g., motion data and/or physical activity data via one of more sensors). In such an example, the mobile device 110 may be configured to monitor a patient for vital signs and the like and the mobile device 110 may communicate such measured patient data to the database 120.

In some implementations, the mobile device 110 may include a mobile computing device having wireless capabilities. A mobile device may refer to any device having a processing system and a mobile power source or supply, such as one or more batteries, for example.

Examples of a mobile device may include a tablet, touch pad, portable computer, handheld computer, palmtop computer, personal digital assistant (PDA), cellular telephone, combination cellular telephone/PDA, smart device (e.g., smart phone, smart tablet, and/or the like), mobile internet device (MID), messaging device, data communication device, and/or the like.

Examples of a mobile device also may include computers that are arranged to be worn by a person, such as a wrist computer, finger computer, ring computer, eyeglass computer, belt-clip computer, arm-band computer, shoe computers, clothing computers, other wearable computers, and/or the like. In embodiments, for example, a mobile computing device may be implemented as a smart phone capable of executing computer applications, as well as voice communications and/or data communications. Although some embodiments may be described with a mobile device implemented as a smart phone by way of example, it may be appreciated that other embodiments may be implemented using other wireless mobile computing devices as well. The embodiments are not limited in this context.

In some implementations, such a mobile device may include a housing, a display, an input/output (I/O) device, an antenna, and/or the like. Such a display may include any suitable display unit for displaying information appropriate for a mobile device. Such an I/O device may include any suitable I/O device for entering information into a mobile device. Examples for such an I/O device may include an alphanumeric keyboard, a numeric keypad, a touch pad, input keys, buttons, switches, rocker switches, microphones, speakers, voice recognition device and software, and/or the like.

Additionally, or alternatively, in a still further example, the personal computer 112 may be utilized to provide input and output for the patient 118 with respect to the CPAP therapy provided by the therapeutic device and/or enter patient data to the database 120. In some implementations, the personal computer 112 may be implemented via one or more form factor devices (e.g., a tablet, a laptop, a workstation, and/or the like).

In another example, the therapeutic device 116 may be utilized to enter patient data to the database 120. For example, the therapeutic device 116 may determine measured patient data. In such an example, the therapeutic device 116 may be configured to monitor the delivery of a particular therapy (e.g., a non-medication treatment) to a patient 118 and may communicate such measured patient data to database 120.

In some implementations, the therapeutic device 116 may supply and/or monitor the administration of a continuous positive airway pressure (CPAP) type therapy.

In the illustrated implementation, the database 120 may include one or more types of patient data. As used herein, the term "database" refers to a collection of data and information organized in such a way as to allow the data and information to be stored, retrieved, updated, and/or manipulated. The term "database" as used herein may also refer to databases that may reside locally or that may be accessed from a remote location (e.g., via remote network servers).

As used herein, the term "patient data" refers to data or information for identifying an individual. Patient data may include measured patient data from an analog medical device, a sensor, a patient monitor, a therapeutic device, a medical management device, a medical imaging device, the like, and/or combinations thereof. Additionally, patient data may include a patient's name, age, weight, previous medical history, admission number, medical personnel in charge, date of admission, medical condition, a medical status, like, and/or combinations thereof.

Additionally, or alternatively, in some implementations, the database 120 may include or be associated with a simulated database. In such an example, such a simulated database may generate estimated patient data (e.g., via a computational model, a pre-trained prediction model, etc.). For example, the simulated database may utilize some measured patient data from the therapeutic device 116, etc. to generate some other estimated patient data. Such a simulated database may utilize digital twin technology to perform the estimation, for example. In such an example, such estimated patient data may be marked to indicate its estimated nature (rather than measured patient data). Additionally, or alternatively, a weight factor may be applied to the estimated patient data so that the estimated patient data may have a lower weight than corresponding measured patient data.

In some implementations, communications are facilitated through the messaging system 122. For example, some or all communications between the central computing system 102 and one or more of the mobile device 110, the personal computer 112, and the therapeutic device 116 are facilitated through the messaging system 122.

As will be described in greater detail below, several different techniques to provide education and feedback that is automatically customized/personalized based on an automatically determined personality type may be implemented in the CPAP therapy management system 100.

Figure 2:
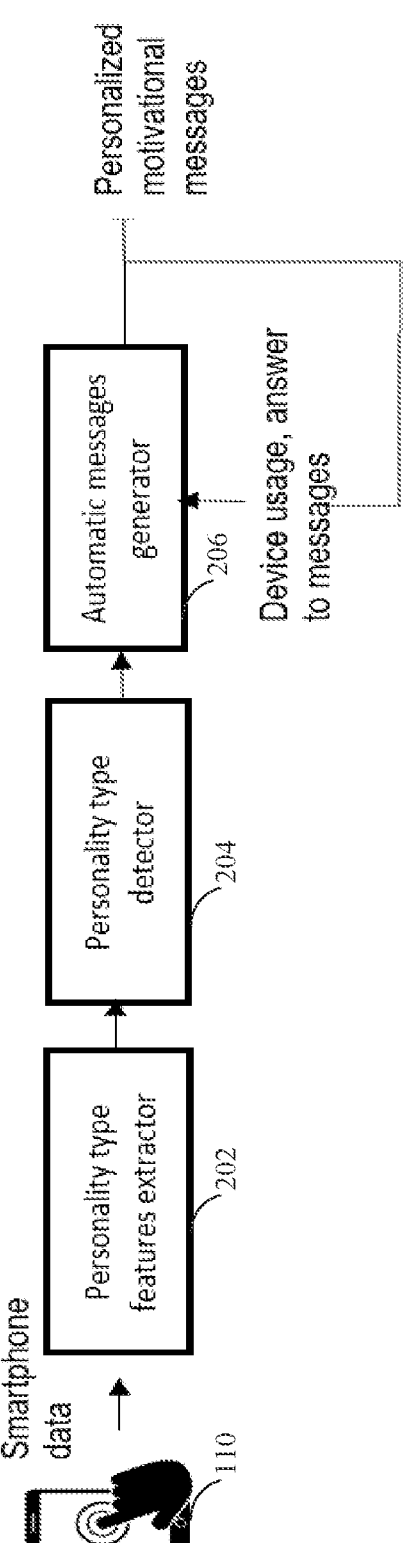
FIG. 2 is a further illustration of a block diagram of portions of an example CPAP therapy management system according to an embodiment.

FIG. 2 shows an example of a further illustration of a block diagram of portions of an example CPAP therapy management system 100 according to an embodiment. As discussed above, in some implementations, procedures are described that: detect user personality from mobile apps usage information and customize and automatically deliver support/motivational messages to user based on their personality type, reaction to initial messages and device usage. As illustrated, the CPAP therapy management system 100 includes a personality type feature extractor 202, a personality type detector 204, and an automatic messages generator 206.

In some implementations, the personality type feature extractor 202 receives input from the mobile device 110. For example, the personality type feature extractor 202 receives mobile apps logs from multiple apps of choice. The personality type feature extractor 202 extracts information from the input from the mobile device 110. For example, the personality type feature extractor 202 extracts features describing mobile apps usage, such as: frequency, time, visualized content, the like, and/or combinations thereof (e.g., accessing articles describing OSA conditions, general knowledge news, social networks, sports, etc.).

In some examples, the personality type detector 204 includes a pretrained classification model. Such a pretrained classification model receives features describing mobile apps usage from the personality type feature extractor 202. The personality type detector 204 provides as output the personality type (e.g., A-B-C-D or the like) based on the pretrained classification model processing the features describing mobile apps usage.

In some implementations, the automatic messages generator 206 receives a personality type of the user from the personality type detector 204. The automatic messages generator 206 define a list of messages to send to the user in response to the received personality type. For example, content, frequency, and/or timing of such messages can be predefined for personality class. Additionally, or alternatively, the content, frequency, and/or timing of such messages can be adapted based on initial usage of the CPAP machine. Additionally, or alternatively, the content, frequency, and/or timing of such messages can be adapted based on patient answer to initial messages during therapy set-up.

Figure 3:
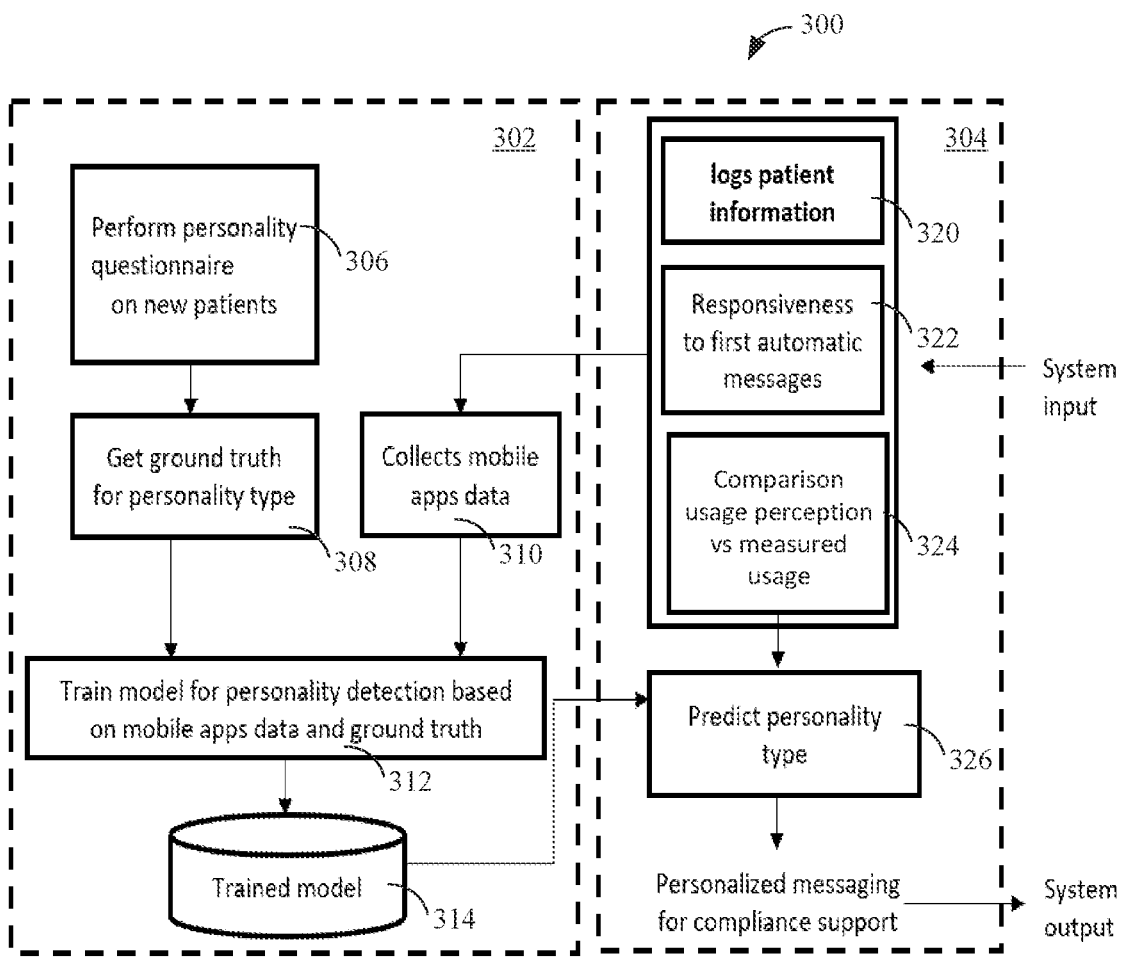
FIG. 3 an illustration of a flowchart of a method for monitoring and/or management of CPAP therapy according to an embodiment.

FIG. 3 shows an example method 300 for training and implementing monitoring and/or management of CPAP therapy according to an embodiment. The method 300 may generally be implemented in a CPAP therapy management system, such as, for example, the CPAP therapy management system 100 (FIG. 1), already discussed.

As will be discussed in greater detail below, illustrated processing block 302 provides for construction of the personality detection system; while, illustrated processing block 304 provides for performance of compliance support messaging based on an individual patient's personality type post-training.

Construction of the Personality Detection System

To train/build one example implementations the following steps are utilized. Illustrated processing block 306 provides for performing a personality questionnaire on a set of new patients. For example, a personality questionnaire (e.g., Eysenck Personality Questionnaire (EPQ) or the like) is given to N (e.g., 50, 200, or some other statistically significant number) newly diagnosed OSA patients that will start CPAP therapy. The questionnaire provides an input to get a personality type reference.

Additionally, or alternatively, a different questionnaire or combinations of questionnaires can be used to assess reference of the personality types of the patients, whose data are used to train the classification model.

A therapy support app is installed on each patient's mobile device.

Illustrated processing block 308 provides for getting a ground truth for the personality type. For example, patient response data may be gathered. In some implementations, the patient response data is based on patient responses during therapy set-up (e.g., initiated on the first day of therapy for a fixed period of time) of the obstructive sleep apnea treatment.

In one implementation, messages will be sent to the user starting on the first day of the therapy and for a fixed period of time (e.g., the seven following days), send messages to the user. Such messages could include:

How have you slept last night in a score 1 to 10?

How many hours have you been using the device last night?

The answer provided by user (e.g., patient responses during therapy set-up) is recorded as well as, if any, an elapsed time from the receiving of the message.

Illustrated processing block 310 provides for collecting smartphone data. For example, smartphone data is collected for a fixed period of time prior to starting the therapy and another period of time after the start of therapy (e.g., for 7 days before starting the therapy and 7 days after starting the therapy). The following are some examples of such smartphone data:

Frequency of use of the therapy support app (e.g., an averaged number of times therapy support app was opened per day.

Type of content visualized in the therapy support app (e.g., articles about OSA, number of hours of CPAP usage, Apnea Index, etc.).

Number of times 'OSA', 'sleep apnea', 'SA' was searched in the browser.

Length of the patient responses during therapy set-up (e.g., answers counted in number of words of the patient to messages sent at the start of therapy).

Tone of voice of the patient responses during therapy set-up (e.g., extracted using Natural Language Processing or the like).

Difference between number of hours of usage measured from device data and number of hours reported by the user.

Motion information (e.g., the number of and types of places visited per day by the patient).

Physical activity information performed by the patient.

In-app interaction data from the patient (e.g., which items have been clicked on, liked/disliked, which items have been skipped, scrolling times, reading times, etc.).

Any other information collected from the smartphone or a combination/aggregation of the other information reported above.

Illustrated processing block 312 provides for training a machine learning model for personality detection based on mobile apps data and ground truth data to output a trained model at illustrated processing block 314. For example, a machine learning model may be trained with a supervised learning approach. Such a supervised learning approach uses as input data the features extracted from smartphone data and the personality type extracted from the personality type questionnaire (e.g., as a reference output). Multiple types of the classification model class could be used as well as multiple types of questionnaires.

Please not that, during construction of the trained model 314, a limited number of patients are being asked to fill in all personality questionnaires, and for the same patients their therapy support data is being logged. The trained model 314 (e.g., an AI model) will be trained on these data to predict for later patients that have not filled in these personality surveys as to what their personality is. Instead, later patients will have their personality advantageously predicted from therapy interaction data only.

Post-Training Performance of Compliance Support Messaging:

As discussed above, illustrated processing block 304 provides for performance of compliance support messaging based on an individual patient's personality type post-training.

Illustrated processing block 320 provides for logging patient information.

Illustrated processing block 322 provides for tracking a patient's responsiveness to the first automatic messages (e.g., at the initiation of therapy and for a fixed time period) to output patient responsiveness data.

Illustrated processing block 324 provides for a comparison of a patient's usage perception as compared to actual measured usage to output device usage data. For example, one aspect that can be used for personality detection of a patient is to check for difference between perceived usage versus real usage of a therapy device. In some implementations, this can be checked by comparing answers from messages sent to the user starting on the first day of the therapy (e.g., as subjective input from patient) with actual sleep/therapy related data from the device (e.g., as objective data).

Illustrated processing block 326 provides for using a predicted personality type to determine a treatment guidance for the patient. For example, such a treatment guidance could include generating one or more messages with a selected content, selected frequency, selected timing done on a personality-type-by-personality-type basis.

Additionally, or alternatively, the device usage data and/or the patient responsiveness data can be utilized to modify the treatment guidance for the patient (e.g., used in addition to the predicted personality type.

In operation, if it is detected that a person has high "internal locus of control" personality's trait and low adherence to therapy is detected, then following message could be sent:

"We have noticed that your adherence to the CPAP therapy is low, but this is not your fault, we will investigate the reasons and help you in improving"

Otherwise, if a person has "external locus of control" personality's trait then messages for emphasizing that the person can influence the situation should sent:

"We have noticed that your adherence to the CPAP therapy is low. You are capable to improve it, we can provide better guidance to help you in increasing the adherence."

Additionally, or alternatively, the extraction of the features for the classification model and the computation of the model output could be performed using the processor of the patient's mobile device or in the cloud. In such an example, the output of the model will be sent to the cloud and used to trigger the generation/selection of the automatic motivational/support messages. Such messages can be delivered as standard text messages, mails, calls or any other mean.

Additionally, or alternatively, data collected from wearable devices such sleep and/or activity trackers can be utilized as additional input of the personality type classification model (e.g., data collected from wearable devices such sleep and/or activity trackers).

Additional and/or alternative operations for method 300 are described in greater detail below in the description of FIG. 4 and/or FIG. 5.

FIG. 4 shows an example method 400 for monitoring and/or management of CPAP therapy according to an embodiment. The method 400 may generally be implemented in a CPAP therapy management system, such as, for example, the CPAP therapy management system 100 (FIG. 1 and/or FIG. 2), already discussed.

Illustrated processing block 402 provides for extracting one or more features describing mobile apps usage. For example, such one or more features describing mobile apps usage may be extracted, via a personality type feature extractor, based on one or more mobile apps logs from a mobile device associated with a patient receiving obstructive sleep apnea treatment.

Illustrated processing block 404 provides for determining a personality type of the patient based on processing the features describing mobile apps usage. For example, such a personality type of the patient may be determined, via a personality type detector, based on processing the features describing mobile apps usage from the personality type feature extractor.

Illustrated processing block 406 provides for determining a treatment guidance for the patient based on the personality type. For example, such a treatment guidance for the patient may be determined, via an automatic messages generator, based on the personality type from the personality type detector.

In some implementations, the treatment guidance includes a first set of messages for the patient in response to a first personality type and a different second set of messages for the patient in response to a different second personality type.

Illustrated processing block 408 provides for communicating the treatment guidance for the patient to the mobile device. For example, the treatment guidance for the patient may be communicated, via the automatic messages generator, to the mobile device associated with the patient receiving obstructive sleep apnea treatment.

In some examples, the methods described herein (e.g., method 400 and/or method 500) may be performed at least in part by cloud processing.

Additional and/or alternative operations for method 400 are described in greater detail below in the description of FIG. 5.

Figure 5:
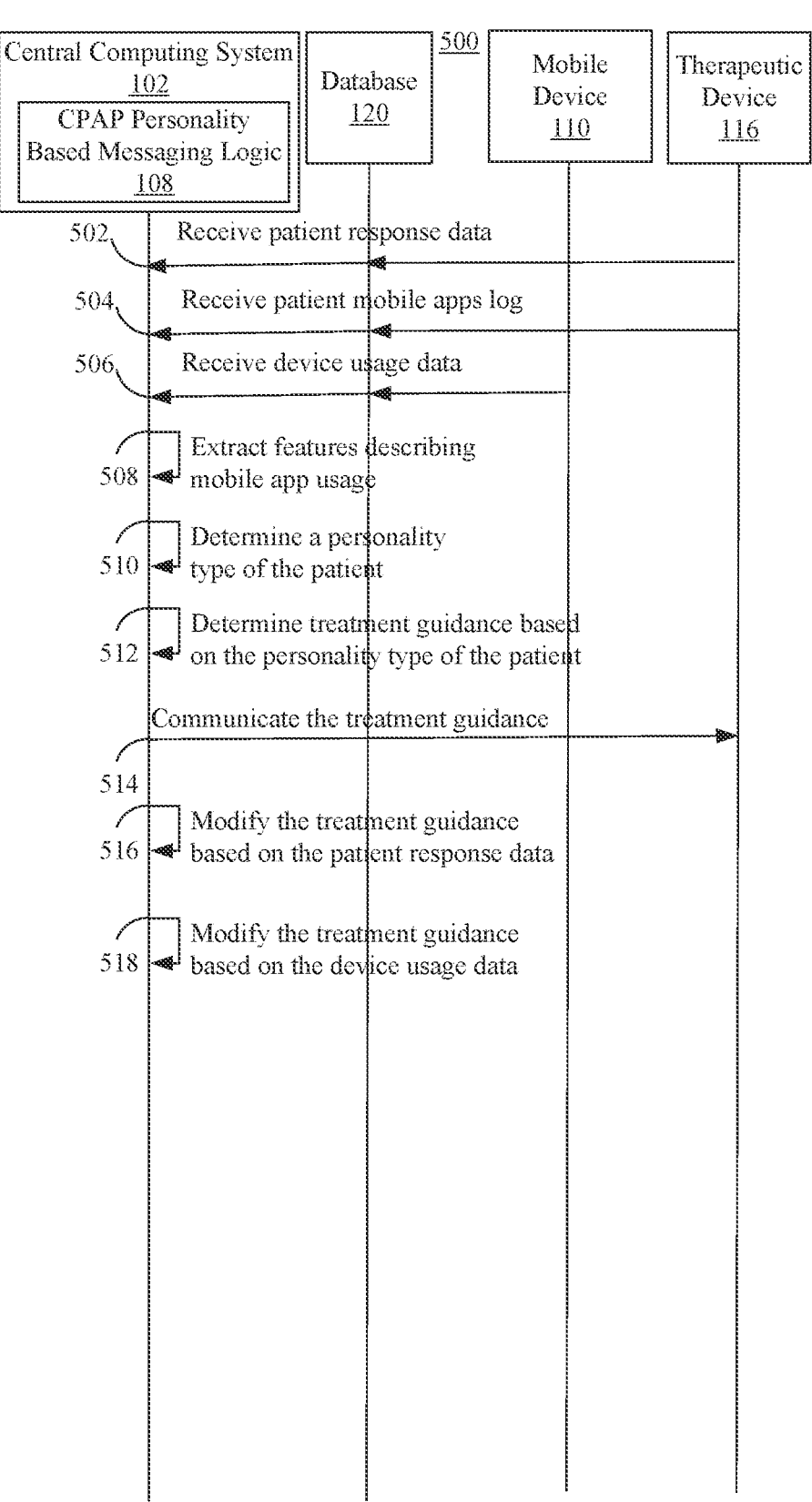
FIG. 5 is an illustration of a flowchart of a still further method for monitoring and/or management of CPAP therapy according to an embodiment.

FIG. 5 is a flowchart of an example of another method 500 for monitoring and/or management of CPAP therapy according to an embodiment. The method 500 may generally be implemented in an CPAP therapy management system, such as, for example, the CPAP therapy management system 100 (FIG. 1 and/or FIG. 2), already discussed.

In an embodiment, the method 500 (as well as method 300 (FIG. 3) and/or method 400 (FIG. 4)) may be implemented in logic instructions (e.g., software), configurable logic, fixed-functionality hardware logic, etc., or any combination thereof. While certain portions of an CPAP therapy management system are illustrated in method 500, other portions of the CPAP therapy management system 100 (FIG. 1) have been intentionally left out to simplify the explanation of the method.

In some examples, it will be appreciated that some or all of the operations in method 500 (as well as method 300 (FIG. 3) and/or method 400 (FIG. 4)) may be performed at least in part by cloud processing.

It will be appreciated that some or all of the operations in method 500 (as well as method 300 (FIG. 3) and/or method 400 (FIG. 4)) are described using a "pull" architecture (e.g., polling for new information followed by a corresponding response) may instead be implemented using a "push" architecture (e.g., sending such information when there is new information to report), and vice versa.

With reference to both FIG. 2 and FIG. 5, illustrated processing block 502 provides for receiving patient response data. For example, such patient response data may be received, via an automatic messages generator 206 (e.g., a part of a CPAP personality based messaging logic 108 on central computing system 102), from the therapeutic device 116 and/or the mobile device 110.

In some implementations, the patient response data is based on patient responses during therapy set-up of the obstructive sleep apnea treatment.

Additionally, or alternatively, such patient response data may be received via a database 120 and passed to the automatic messages generator 206 from the therapeutic device 116.

Illustrated processing block 504 provides for receiving one or more mobile apps logs of one or more mobile apps from a mobile device. For example, such one or more mobile apps logs of one or more mobile apps may be received, via a personality type feature extractor 202 (e.g., a part of a CPAP personality based messaging logic 108 on central computing system 102), from a mobile device 110 associated with a patient receiving obstructive sleep apnea treatment.

Additionally, or alternatively, such one or more mobile apps logs of one or more mobile apps may be received via a database 120 and passed to the automatic messages generator 206 from the therapeutic device 116.

Illustrated processing block 506 provides for receiving device usage data. For example, device usage data may be received, via the automatic messages generator 206, from a therapeutic device 116.

Additionally, or alternatively, such device usage data may be received via a database 120 and passed to the automatic messages generator 206 from the therapeutic device 116.

Illustrated processing block 508 provides for extracting one or more features describing mobile apps usage. For example, such one or more features describing mobile apps usage may be extracted, via the personality type feature extractor 202, based on the one or more mobile apps logs.

In some implementations, the features describing mobile apps usage include frequency, time, visualized content, the like, and/or combinations thereof.

In some implementations, the features describing mobile apps usage may be received, via the personality type detector 204, from the personality type feature extractor 202.

Illustrated processing block 510 provides for determining a personality type of the patient based on processing the features describing mobile apps usage. For example, such a personality type of the patient may be determined, via a personality type detector 204 (e.g., a part of a CPAP personality based messaging logic 108 on central computing system 102), based on processing the features describing mobile apps usage from the personality type feature extractor.

In some examples, the personality type detector 204 includes a pretrained classification model. In such examples, the determination of the personality type is based on processing the features describing mobile apps usage utilizing the pretrained classification model. Additional discussion of such a pretrained classification model can be found in the description above regarding FIG. 3.

In some implementations, the personality type of the patient may be received, via the automatic messages generator 206, from the personality type detector 204.

Illustrated processing block 512 provides for determining treatment guidance for the patient based on the personality type. For example, such treatment guidance for the patient may be determined, via the automatic messages generator 206, based on the personality type.

In some examples, the treatment guidance includes a first set of messages for the patient in response to a first personality type and a different second set of messages for the patient in response to a different second personality type.

In some implementations, the operation to determine the treatment guidance includes determination of one or more of a first content, a first frequency, or a first timing associated with the first set of messages in response to the first personality type and one or more of a different second content, a different second frequency, or a different second timing associated with the different second set of messages in response to the different second personality type.

Illustrated processing block 514 provides for communicating the treatment guidance for the patient to the mobile device 110. For example, the treatment guidance for the patient may be communicated, via the automatic messages generator 206, to the mobile device 110 associated with the patient receiving obstructive sleep apnea treatment.

Illustrated processing block 516 provides for modifying the treatment guidance based on the patient response data. For example, the treatment guidance may be modified, via the automatic messages generator 206, based on the patient response data.

In some implementations, the operation to modify the treatment guidance includes modification one or more of the first content, the first frequency, or the first timing associated with the first set of messages in response to the first personality type and one or more of the different second content, the different second frequency, or the different second timing associated with the different second set of messages in response to the different second personality type based on the patient response data.

Illustrated processing block 518 provides for modifying the treatment guidance based on the device usage data. For example, the treatment guidance may be modified, via the automatic messages generator 206, based on the device usage data.

In some implementations, the operation to modify the treatment guidance includes modification one or more of the first content, the first frequency, or the first timing associated with the first set of messages in response to the first personality type and one or more of the different second content, the different second frequency, or the different second timing associated with the different second set of messages in response to the different second personality type based on the device usage data.

Figures 6, 7, 8:
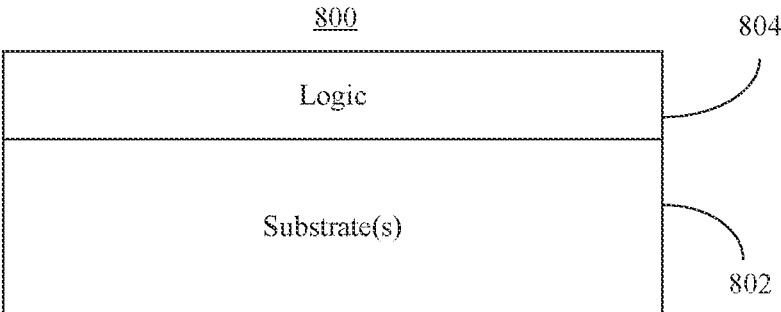
FIG. 6 is an illustration of a block diagram of a computer program product according to an embodiment.
FIG. 7 is a further illustration of a therapy management system according to an embodiment.
FIG. 8 is an illustration of a hardware apparatus including a semiconductor package according to an embodiment.

FIG. 6 illustrates a block diagram of an example computer program product 600. In some examples, as shown in FIG.

6, computer program product 600 includes a machine-readable storage 602 that may also include logic 604. In some implementations, the machine-readable storage 602 may be implemented as a non-transitory machine-readable storage. In some implementations the logic 604 may be implemented as machine-readable instructions, such as software, for example. In an embodiment, the logic 604, when executed, implements one or more aspects of the method 300 (FIG. 3), the method 400 (FIG. 4), the method 500 (FIG. 5), and/or realize the CPAP therapy management system 100 (FIG. 1 and/or FIG. 2), already discussed.

FIG. 7 shows an illustrative example of the CPAP therapy management system 100. In the illustrated example, the CPAP therapy management system 100 may include a processor 702 and a memory 704 communicatively coupled to the processor 702. The memory 704 may include logic 706 as a set of instructions. In some implementations the logic 706 may be implemented as software. In an embodiment, the logic 706, when executed by the processor 702, implements one or more aspects of the method 300 (FIG. 3), the method 400 (FIG. 4), the method 500 (FIG. 5), and/or realize the CPAP therapy management system 100 (FIG. 1 and/or FIG. 2), already discussed.

In some implementations, the processor 702 may include a general purpose controller, a special purpose controller, a storage controller, a storage manager, a memory controller, a micro-controller, a general purpose processor, a special purpose processor, a central processor unit (CPU), the like, and/or combinations thereof.

Further, implementations may include distributed processing, component/object distributed processing, parallel processing, the like, and/or combinations thereof. For example, virtual computer system processing may implement one or more of the methods or functionalities as described herein, and the processor 702 described herein may be used to support such virtual processing.

In some examples, the memory 704 is an example of a computer-readable storage medium. For example, memory 704 may be any memory which is accessible to the processor 702, including, but not limited to RAM memory, registers, and register files, the like, and/or combinations thereof. References to "computer memory" or "memory" should be interpreted as possibly being multiple memories. The memory may for instance be multiple memories within the same computer system. The memory may also be multiple memories distributed amongst multiple computer systems or computing devices.

FIG. 8 shows an illustrative semiconductor apparatus 800 (e.g., chip and/or package). The illustrated apparatus 800 includes one or more substrates 802 (e.g., silicon, sapphire, or gallium arsenide) and logic 804 (e.g., configurable logic and/or fixed-functionality hardware logic) coupled to the substrate(s) 802. In an embodiment, the logic 804 implements one or more aspects of the method 300 (FIG. 3), the method 400 (FIG. 4), the method 500 (FIG. 5), and/or realize the CPAP therapy management system 100 (FIG. 1 and/or FIG. 2), already discussed.

In some implementations, logic 804 may include transistor array and/or other integrated circuit/IC components. For example, configurable logic and/or fixed-functionality hardware logic implementations of the logic 804 may include configurable logic such as, for example, programmable logic arrays (PLAs), field programmable gate arrays (FPGAs), complex programmable logic devices (CPLDs), or fixed-functionality logic hardware using circuit technology such as, for example, application specific integrated circuit (ASIC), complementary metal oxide semiconductor (CMOS) or transistor-transistor logic (TTL) technology, the like, and/or combinations thereof.

All definitions, as defined and used herein, should be understood to control over dictionary definitions, definitions in documents incorporated by reference, and/or ordinary meanings of the defined terms.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. The term "coupled" may be used herein to refer to any type of relationship, direct or indirect, between the components in question, and may apply to electrical, mechanical, fluid, optical, electromagnetic, electromechanical, or other connections. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components.

In the claims, as well as in the specification above, the terms "first", "second", etc. may be used herein only to facilitate discussion, and carry no particular temporal or chronological significance unless otherwise indicated.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

The indefinite articles "a" and "an," as used herein in the specification and in the claims, unless clearly indicated to the contrary, should be understood to mean "at least one."

As used herein, the term "or" or "and/or" is inclusive and not exclusive, unless expressly indicated otherwise or indicated otherwise by context. Therefore, herein, "A or B" means "A, B, or both," unless expressly indicated otherwise or indicated otherwise by context. Moreover, "and" is both joint and several, unless expressly indicated otherwise or indicated otherwise by context. Therefore, herein, "A and B" means "A and B, jointly or severally," unless expressly indicated otherwise or indicated otherwise by context.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

As used in this application and in the claims, a list of items joined by the term "one or more of" may mean any combination of the listed terms. For example, the phrases "one or more of A, B or C" may mean A; B; C; A and B; A and C; B and C; or A, B and C.

As is described above in greater detail, one or more processor, other unit, the like, and/or combinations thereof may fulfill the functions of several items recited in the claims.

As is described above in greater detail, a computer program may be stored/distributed on a suitable medium, such as an optical storage medium or a solid-state medium supplied together with or as part of other hardware, but may also be distributed in other forms, such as via the Internet or other wired or wireless telecommunication systems.

It should also be understood that, unless clearly indicated to the contrary, in any methods discussed herein that include more than one step or act, the order of the steps or acts of the method is not necessarily limited to the order in which the steps or acts of the method are recited. Further, such methods may include additional or alternative steps or acts.

As used in the claims, the mere fact that certain measures are recited in mutually different dependent claims does not indicate that a combination of these measured cannot be used to advantage.

It is also noted that the claims may include reference signs/numerals in accordance with PCT Rule 6.2(b). However, the present claims should not be considered to be limited to the exemplary embodiments corresponding to the reference signs/numerals.

Those skilled in the art will appreciate from the foregoing description that the broad techniques of the embodiments of the present invention can be implemented in a variety of forms. Therefore, while the embodiments of this invention have been described in connection with particular examples thereof, the true scope of the embodiments of the invention should not be so limited since other modifications will become apparent to the skilled practitioner upon a study of the drawings, specification, and following claims.

The invention claimed is:

1. A therapy management system, comprising:
   a processor; and
   a memory communicatively coupled to the processor, the memory storing logic that includes a set of instructions executable by the processor, which when executed by the processor, cause the processor to:
   automatically extract, via a personality type feature extractor, one or more features describing mobile apps usage based on one or more mobile apps logs from a mobile device associated with a patient receiving obstructive sleep apnea treatment, wherein the features describing mobile apps usage comprise one or more of: usage frequency, usage time, or usage visualized content, browser search terms relating to obstructive sleep apnea, in app interaction data, motion or physical activity information, and characteristics of patient responses during therapy setup including at least response latency, response length, and linguistic tone extracted via natural language processing;
   determine, via a personality type detector that comprises a pretrained classification model, a personality type of the patient based on processing the one or more features describing mobile apps usage from the personality type feature extractor utilizing the pretrained classification model, the pretrained classification model having been trained via supervised learning using, as inputs, features extracted from smartphone data and, as labels, personality types obtained from a personality questionnaire;
   determine, via an automatic messages generator, a treatment guidance for the patient based on the personality type, wherein the treatment guidance comprises a first set of messages for the patient in response to a first personality type and a second set of messages for the patient in response to a different second personality type,
   wherein the second set of messages is different than the first set of messages, and wherein the automatic messages generator modifies one or more of the content, frequency, and timing of the messages based on device usage data from a therapeutic device and patient response data during therapy setup, including comparing perceived usage reported by the patient to actual usage measured by the therapeutic device and updating subsequent messages upon detecting a discrepancy between the perceived usage and the measured usage and based on a measured response latency during therapy setup; and
   communicate, via the automatic messages generator, the treatment guidance for the patient to the mobile device associated with the patient receiving obstructive sleep apnea treatment.

2. The therapy management system of claim 1, wherein the set of instructions, which when executed by the processor, cause the processor further to: receive, via the personality type feature extractor, one or more mobile apps logs of one or more mobile apps from the mobile device; receive, via the personality type detector, the features describing mobile apps usage from the personality type feature extractor; and receive, via the automatic messages generator, the personality type of the patient from the personality type detector.

3. The therapy management system of claim 1, wherein the operation to determine the treatment guidance comprises determination of one or more of a first content, a first frequency, or a first timing associated with the first set of messages in response to the first personality type and one or more of a different second content, a different second frequency, or a different second timing associated with the different second set of messages in response to the different second personality type.

4. The therapy management system of claim 3, wherein the set of instructions, which when executed by the processor, cause the processor further to: receive, via the automatic messages generator, device usage data from a therapeutic device; and modify, via the automatic messages generator, the treatment guidance based on the device usage data, wherein the operation to modify the treatment guidance comprises modification of one or more of the first content, the first frequency, or the first timing associated with the first set of messages in response to the first personality type and one or more of the different second content, the different second frequency, or the different second timing associated with the different second set of messages in response to the different second personality type based on the device usage data.

5. The therapy management system of claim 3, wherein the set of instructions, which when executed by the processor, cause the processor further to: receive, via the automatic messages generator, patient response data from one or more of the therapeutic device or the mobile device; and modify, via the automatic messages generator, the treatment guidance based on the patient response data, wherein the patient response data is based on patient responses during therapy set-up of the obstructive sleep apnea treatment, wherein the operation to modify the treatment guidance comprises modification of one or more of the first content, the first frequency, or the first timing associated with the first set of messages in response to the first personality type and one or more of the different second content, the different second frequency, or the different second timing associated with the different second set of messages in response to the different second personality type based on the patient response data.

6. A non-transitory computer readable medium, having stored thereon a set of instructions, which when executed by a computing device, cause the computing device to: automatically extract, via a personality type feature extractor, one or more features describing mobile apps usage based on one or more mobile apps logs from a mobile device associated with a patient receiving obstructive sleep apnea treatment, wherein the features describing mobile apps usage comprise one or more of: usage frequency, usage time, or usage visualized content, browser search terms relating to obstructive sleep apnea, in app interaction data, motion or physical activity information, and characteristics of patient responses during therapy setup including at least response latency, response length, and linguistic tone extracted via natural language processing; determine, via a personality type detector that comprises a pretrained classification model, a personality type of the patient based on processing the one or more features describing mobile apps usage from the personality type feature extractor utilizing the pretrained classification model, the pretrained classification model having been trained via supervised learning using, as inputs, features extracted from smartphone data and, as labels, personality types obtained from a personality questionnaire; determine, via an automatic messages generator, a treatment guidance for the patient based on the personality type, wherein the treatment guidance comprises a first set of messages for the patient in response to a first personality type and a second set of messages for the patient in response to a different second personality type, wherein the second set of messages is different than the first set of messages, and wherein the automatic messages generator modifies one or more of the content, frequency, and timing of the messages based on device usage data from a therapeutic device and patient response data during therapy setup, including comparing perceived usage reported by the patient to actual usage measured by the therapeutic device and updating subsequent messages upon detecting a discrepancy between the perceived usage and the measured usage and based on a measured response latency during therapy setup; and communicate, via the automatic messages generator, the treatment guidance for the patient to the mobile device associated with the patient receiving obstructive sleep apnea treatment.

7. The non-transitory computer readable medium of claim 6, wherein the set of instructions, which when executed by the computing device, cause the computing device further to: receive, via the personality type feature extractor, one or more mobile apps logs of one or more mobile apps from the mobile device; receive, via the personality type detector, the features describing mobile apps usage from the personality type feature extractor; and receive, via the automatic messages generator, the personality type of the patient from the personality type detector.

8. The non-transitory computer readable medium of claim 6, wherein the operation to determine the treatment guidance comprises determination of one or more of a first content, a first frequency, or a first timing associated with the first set of messages in response to the first personality type and one or more of a different second content, a different second frequency, or a different second timing associated with the different second set of messages in response to the different second personality type.

9. The non-transitory computer readable medium of claim 8, wherein the set of instructions, which when executed by the computing device, cause the computing device further to: receive, via the automatic messages generator, device usage data from a therapeutic device; and modify, via the automatic messages generator, the treatment guidance based on the device usage data, wherein the operation to modify the treatment guidance comprises modification of one or more of the first content, the first frequency, or the first timing associated with the first set of messages in response to the first personality type and one or more of the different second content, the different second frequency, or the different second timing associated with the different second set of messages in response to the different second personality type based on the device usage data.

10. The non-transitory computer readable medium of claim 8, wherein the set of instructions, which when executed by the computing device, cause the computing device further to: receive, via the automatic messages generator, patient response data from one or more of the therapeutic device or the mobile device; and modify, via the automatic messages generator, the treatment guidance based on the patient response data, wherein the patient response data is based on patient responses during therapy set-up of the obstructive sleep apnea treatment, wherein the operation to modify the treatment guidance comprises modification of one or more of the first content, the first frequency, or the first timing associated with the first set of messages in response to the first personality type and one or more of the different second content, the different second frequency, or the different second timing associated with the different second set of messages in response to the different second personality type based on the patient response data.

11. A therapy management method, comprising: automatically extracting via a personality type feature extractor, one or more features describing mobile apps usage based on one or more mobile apps logs from a mobile device associated with a patient receiving obstructive sleep apnea treatment, wherein the features describing mobile apps usage comprise one or more of: usage frequency, usage time, or usage visualized content, browser search terms relating to obstructive sleep apnea, in app interaction data, motion or physical activity information, and characteristics of patient responses during therapy setup including at least response latency, response length, and linguistic tone extracted via natural language processing; determining, via a personality type detector that comprises a pretrained classification model, a personality type of the patient based on processing the one or more features describing mobile apps usage from the personality type feature extractor utilizing the pretrained classification model, the pretrained classification model having been trained via supervised learning using, as inputs, features extracted from smartphone data and, as labels, personality types obtained from a personality questionnaire; determining, via an automatic messages generator, a treatment guidance for the patient based on the personality type, wherein the treatment guidance comprises a first set of messages for the patient in response to a first personality type and a second set of messages for the patient in response to a different second personality type, wherein the second set of messages is different than the first set of messages, and wherein the automatic messages generator modifies one or more of the content, frequency, and timing of the messages based on device usage data from a therapeutic device and patient response data during therapy setup, including comparing perceived usage reported by the patient to actual usage measured by the therapeutic device and updating subsequent messages upon detecting a discrepancy between the perceived usage and the measured usage and based on a measured response latency during therapy setup; and communicating, via the automatic messages generator, the treatment guidance for the patient to the mobile device associated with the patient receiving obstructive sleep apnea treatment.

12. The therapy management method of claim 11, wherein the operation to determine the treatment guidance comprises determination of one or more of a first content, a first frequency, or a first timing associated with the first set of messages in response to the first personality type and one or more of a different second content, a different second frequency, or a different second timing associated with the different second set of messages in response to the different second personality type.

13. The therapy management method of claim 12, further comprising: receiving, via the automatic messages generator, device usage data from a therapeutic device; and modi-fying, via the automatic messages generator, the treatment guidance based on the device usage data, wherein the operation to modify the treatment guidance comprises modification of one or more of the first content, the first frequency, or the first timing associated with the first set of messages in response to the first personality type and one or more of the different second content, the different second frequency, or the different second timing associated with the different second set of messages in response to the different second personality type based on the device usage data.

14. The therapy management method of claim 12, further comprising: receiving, via the automatic messages generator, patient response data from one or more of a therapeutic device or the mobile device; and modifying, via the automatic messages generator, the treatment guidance based on the patient response data, wherein the patient response data is based on patient responses during therapy set-up of the obstructive sleep apnea treatment, wherein the operation to modify the treatment guidance comprises modification of one or more of the first content, the first frequency, or the first timing associated with the first set of messages in response to the first personality type and one or more of the different second content, the different second frequency, or the different second timing associated with the different second set of messages in response to the different second personality type based on the patient response data.

* * * * *